(12) United States Patent
Tsai et al.

(10) Patent No.: US 8,728,009 B2
(45) Date of Patent: May 20, 2014

(54) BIOSENSOR WITH FINGER-POSITIONING FUNCTION

(75) Inventors: Hsin-Yu Tsai, New Taipei (TW); Li-Wei Yu, Kaohsiung (TW); Lung-Te Pan, New Taipei (TW)

(73) Assignee: BroadMaster Biotech Corp., New Taipei (TW)

( * ) Notice: Subject to any disclaimer, the term of this patent is extended or adjusted under 35 U.S.C. 154(b) by 161 days.

(21) Appl. No.: 13/429,230

(22) Filed: Mar. 23, 2012

(65) Prior Publication Data

US 2013/0253287 A1    Sep. 26, 2013

(51) Int. Cl.
   *A61B 5/00*   (2006.01)

(52) U.S. Cl.
   USPC ........................................................ 600/583

(58) Field of Classification Search
   USPC .......... 600/309, 310, 316, 322, 323, 365, 583
   See application file for complete search history.

(56) References Cited

U.S. PATENT DOCUMENTS

| | | | | |
|---|---|---|---|---|
| 5,438,201 A | * | 8/1995 | Rosenthal et al. | 250/341.1 |
| 6,571,114 B1 | * | 5/2003 | Koike et al. | 600/323 |
| 6,679,852 B1 | * | 1/2004 | Schmelzelsen-Redeker et al. | 600/583 |
| 6,687,521 B2 | * | 2/2004 | Sato et al. | 600/344 |
| 6,975,891 B2 | * | 12/2005 | Pawluczyk | 600/310 |
| 7,238,160 B2 | * | 7/2007 | Taniike et al. | 600/583 |
| 7,333,186 B2 | * | 2/2008 | Oshima et al. | 356/39 |
| 8,306,595 B2 | * | 11/2012 | Osaki et al. | 600/322 |
| 8,357,107 B2 | * | 1/2013 | Draudt et al. | 600/584 |
| 8,427,817 B2 | * | 4/2013 | Lewis et al. | 361/679.02 |

* cited by examiner

*Primary Examiner* — Max Hindenburg
(74) *Attorney, Agent, or Firm* — Muncy, Geissler, Olds & Lowe, P.C.

(57) ABSTRACT

The present invention provides a biosensor with finger-positioning function, comprising: a bottom plate, a cover, and a test-strip socket; wherein the cover mounted on the bottom plate has a front end provided with a guiding plate for positioning a finger, and the guiding plate has a center line and a guiding surface, in which the center line passes through a center of the guiding surface; and the test-strip socket is formed at the front end of the cover. When using the biosensor, the user can rest his/her wrist and palm on the cover of the biosensor and rest the punctured finger on the guiding surface provided at the front end of the cover to align the test strip with the blood drop on the finger so as to simplify the measurement.

11 Claims, 3 Drawing Sheets

BIOSENSOR WITH FINGER-POSITIONING FUNCTION

BACKGROUND OF THE INVENTION

1. Technical Field

The present invention relates to biosensors, and more particularly to a biosensor having a feature for positioning a finger.

2. Description of Related Art

With the rapid economic development and the change of modern people's lifestyle and dietary patterns, the global prevalence of diabetes has dramatically increased and diabetes has posed as one of the top challenges to the medical science. Diabetes is known as a chronic disease that cannot be cured completely but can only be effectively controlled to prevent complex complications caused thereby. Thus, for achieving good control of diabetes, a diabetic is always required to monitor his or her blood sugar level regularly.

Currently, using biosensors to measure blood sugar level is one of the most popular ways for diabetics to record and thereby monitor their blood sugar levels every day. As such biosensors, many glucose meters, for example, measure blood sugar levels by way of electrochemical method in recent years. The electrochemical method involves using electrodes and immobilized glucose oxidase or glucose dehydrogenase. Operation of a conventional glucose meter working upon this method typically includes the following steps. First, a test strip is inserted into the glucose meter to turn on the glucose meter automatically. Then a user uses a disposable blood lancet or a blood-sampling pen equipped with a blood lancet to puncture one fingertip and squeeze the finger to raise a drop of blood. Afterward, using his/her free hand, the user holds the glucose meter with the test strip installed, and aligns the window of the test strip with the drop of blood on his/her finger. As a result, the test strip absorbs the blood by capillarity and the enzyme-containing reagent therein reacts with the glucose in the blood to generate an electric current that is then converted by the glucose meter into a reading representing the blood sugar level and displayed at the screen of the glucose meter.

While the conventional glucose meter is easy to use and provides accurate measurement, a significant disadvantage thereof exists because the user needs to hold the glucose meter and aligns the window of the test strip precisely with the punctured, blood-oozing finger. To some aged people suffering from, for example, presbyopia or Parkinson's disease, or people having poor hand-eye coordination, it would be very difficult to align the small blood drop on one finger with the narrow test strip (typically having a width smaller than 1 centimeter) in the other hand, and once the user fails in alignment or moves his or her finger, the blood on the finger may fall and cause contamination. Thus, the conventional glucose meter needs to be improved.

Hence, it would be desired to have an improved biosensor that allows users to operate it with a single hand, or enables people with poor eyesight or with hand tremor to use it easily and conveniently.

SUMMARY OF THE INVENTION

In view of the shortcomings of the prior art, the inventor devises a biosensor that enables single-hand operation and has a finger-positioning function. With the finger-positioning function of the disclosed biosensor, a user having his/her finger punctured by a blood lancet just needs to simply lay the finger on the biosensor placed on a tabletop, and the finger can be aligned with the test strip to let the test strip absorb the blood drop on the finger. Thus, the user needs not to hold the biosensor with the other hand and manually align the test strip with the blood drop on the finger.

Therefore, one aspect of the invention is to provide a biosensor with finger-positioning function, characterized in that the biosensor comprising: a bottom plate, a cover and a test-strip socket, wherein the cover mounted on the bottom plate has a front end provided with a guiding plate for positioning a finger, and the guiding plate has a center line and a guiding surface, in which the center line passes through a center of the guiding surface; and the test-strip socket is formed at the front end of the cover.

In an embodiment of the present invention, the test-strip socket is formed on the center line of the guiding plate.

In virtue of the unique design, after the biosensor receives a test strip at its test-strip socket and automatically starts, it can be placed on a tabletop and get ready to perform measurement. Then a user, who use a disposable blood lancet or a blood-sampling pen equipped with a blood lancet to puncture his/her finger and squeezing the finger to raise a drop of blood, can rest his/her wrist and palm on the cover of the biosensor and use the guiding surface provided at the front end of the cover to properly position the punctured finger.

In one preferred embodiment, the guiding surface is inclined from the guiding plate toward the test-strip socket, so as to guide the punctured finger to align with the test strip. The cover has its front end formed with a depressed guiding plate and two sides of the guiding plate form an aligning feature. Preferably, the aligning feature are symmetrical angled structures at two sides for the finger to sit, so that the finger can be easily aligned with the test strip despite hand tremor or other reasons that otherwise hinder the bare alignment. In the preferred embodiment of the present invention, since the guiding plate is for facilitating the alignment between the finger and the test strip, the guiding surface of the guiding plate is better limited in width to an extent that allows it to fittingly receive a single human finger. In particular, the width of the guiding surface is preferably of 1 to 3 centimeters; more preferably about 2 centimeters; and most preferably about 1.5 centimeters.

In one embodiment of the present invention, the guiding plate further includes an audio output, the audio output serves to display audio instructions based on an audio carrier or a chip loaded with audio files and audio drivers installed in the biosensor, thereby voicefully guiding the user to operate the biosensor by following the prerecorded step-by-step instructions.

In another preferred embodiment of the present invention, a removable chassis is deposited below the test-strip socket of the biosensor body. In the event that the user bleeds much, the removable chassis serves to receive the excessive blood and prevents the blood from contaminating the environment. The chassis receiving the blood can then be removed from the disclosed biosensor and cleaned easily.

In another preferred embodiment of the present invention, the cover of the biosensor further comprises a USB connecting port through which the user's individual blood sugar levels can be transmitted to a personal computer, a remote monitoring system hosted by a medical service provider or other blood-sugar management application for graphically showing the user's blood-sugar profile.

DETAILED DESCRIPTION OF THE INVENTION

The following examples are provided to aid those skilled in the art in practicing the present invention. Even so, the examples should not be construed to unduly limit the present invention as modifications and variations in the embodiments discussed herein may be made by those having ordinary skill in the art without departing from the spirit or scope of the present inventive discovery.

Figure 1:
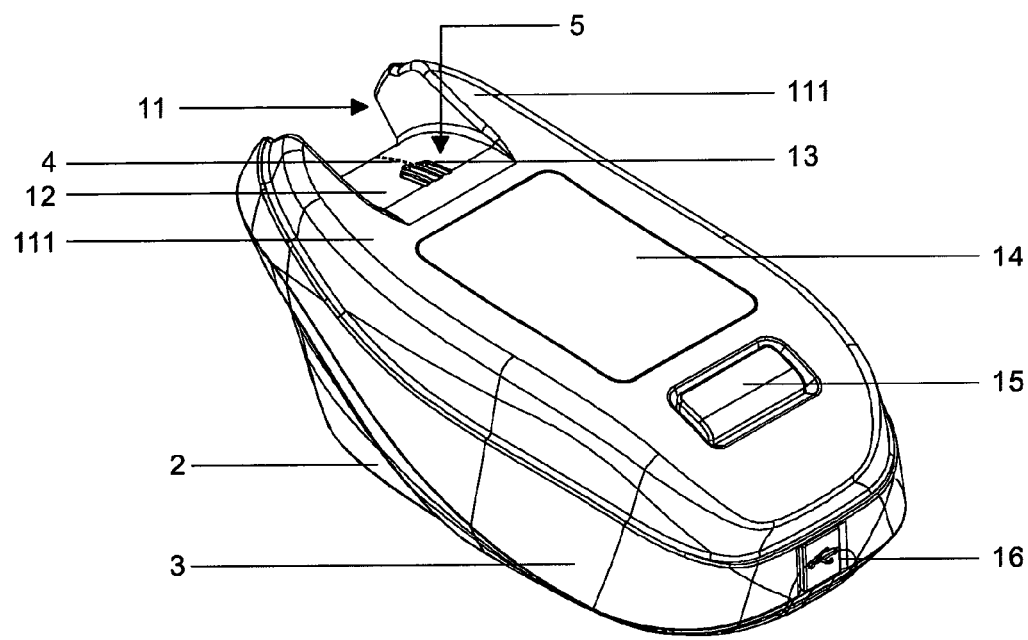
FIG. 1 is a perspective oblique view of the biosensor of the present invention.
Figure 2:
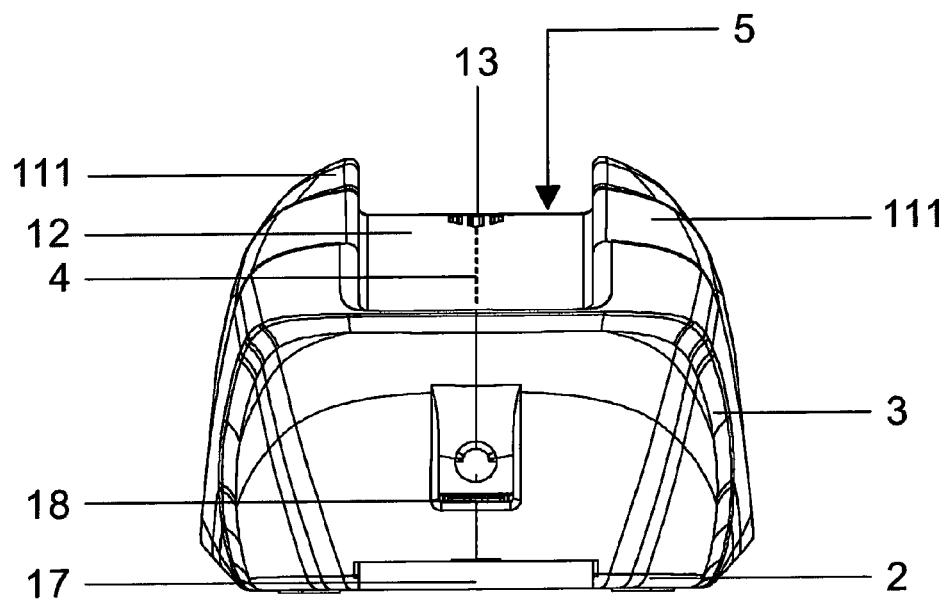
FIG. 2 is a front view of the biosensor of the present invention.

Please first refer to FIG. 1, a perspective oblique view of a biosensor 10 according to one embodiment of the present invention, and FIG. 2, a front view of the biosensor 10. As can be seen in FIG. 1, the biosensor 10 of the present invention comprises a bottom plate 2, a cover 3, and a test-strip socket 18. The cover 3 mounted on and covers the bottom plate 2 forms the body of the biosensor 10 with the bottom plate 2. The cover 3 has a display screen 14 for displaying blood-sugar level, dates, times and/or the test strip's status, and a press button 15 by operating which a user can input individual information, turn on the power, set dates and/or times and/or change individual information. The test-strip socket 18 serves to receive a test strip so that when the test strip absorbs blood, the enzyme in the blood reacts with the test strip for glucose oxidase test, so that a microprocessor installed in the biosensor 10 can analyze the current variation in the test strip in terms of blood sugar level to display the results as blood-sugar level in the display screen 14.

As used herein, the term "the front end of the cover" refers to the end of the biosensor 10 having the test-strip socket 18, and the term "the rear end of the cover" refers to the other end of the biosensor 10 opposite to the end having the test-strip socket 18. When using the biosensor 10 of the present invention, a user is supposed to have his/her palm resting on the rear end of the cover 3 of the biosensor 10 and have his/her fingers resting on the front end of the cover 3 of the biosensor 10.

As used herein, the term "center line" refers to a virtual line in a plane, wherein the virtual line is at the center of the plane and two sides of the plane along the virtual line are substantially symmetrical. In the present invention, the center line 4 of the guiding surface 12 and the center line 4 of the cover 3 are coincident, meaning that the guiding surface 12 is located at the center of the cover 3 and the both have the same center line 4. Each of the guiding surface 12 and the cover 3 may be regarded as being divided into two equal parts by the virtual center line 4, and the two equal parts are substantially the mirror image of each other. As used herein, the term "substantially symmetrical" refers to a state that when all the unnecessary components are ignored, the two sides across the center line 4 are symmetrical. For example, when ignore a structure (i.e. a USB connecting port) or a pattern that is only provided at one side of the cover 3 but not the both sides of the cover 3, the two sides of the cover 3 across the center line 4 are structurally symmetrical.

The following description will be directed to other details of the biosensor 10 of the present invention. Referring to FIG. 1, the guiding surface 12 of the biosensor 10 is an inclined surface inclined from the guiding plate toward the test-strip socket 18, as an inclined surface of a slide. Thereby, the punctured finger may rest on the guiding surface 12 and incline toward the test-strip socket 18. Since the cover 3 has its front end provided with the guiding plate 5, two sides of the guiding plate 5 form an aligning feature 11. The aligning feature 11 may be of any shape, but preferably formed as angled structures that are transversely symmetrical.

Figure 3:
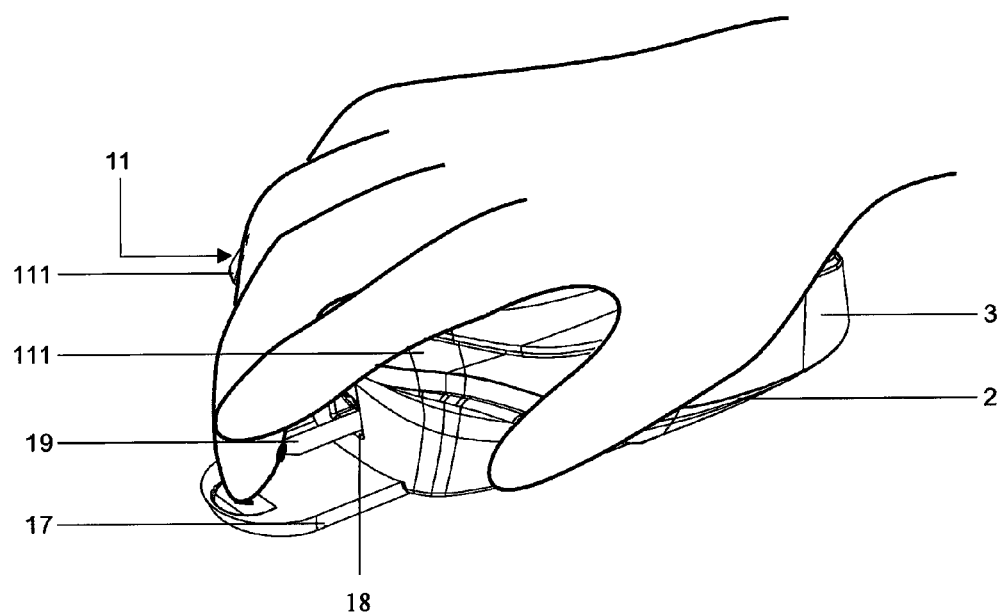
FIG. 3 is an applied view of the biosensor of the present invention.

Now referring to the applied view of the biosensor 10 as shown in FIG. 3, the biosensor 10 receiving a test strip 19 at its test-strip socket 18 and then automatically starting is placed on a tabletop with its bottom plate 2 supported by the tabletop. At this time, a user using a disposable blood lancet or a blood-sampling pen equipped with a blood lancet to puncture one of his/her fingers and squeezing the punctured finger to raise a drop of blood. The user then simply places his/her palm on the rear end of the cover 3 and rests the punctured finger on the front of the cover 3, without manually holding the biosensor 10 with the other hand. Consequently, the punctured finger (the middle finger as depicted) resting on the front end of the cover 3 of the biosensor 10 can be guided by the guiding surface 12 to align with the test strip 19. Meanwhile, the aligning feature 11 formed at the two sides of the guiding surface 12 can facilitate positioning of the punctured finger. Since the test-strip socket 18 is deposited at the front end of the cover 3 and extending along the center line 4 of the guiding plate 5, when the middle finger resting on the guiding surface 12 is punctured at the center of the fingertip, the user can easily bend or stretch the middle finger to make the point and thereby the blood drop properly aligned with a window opened to the test strip 19, thereby allowing blood absorption, reaction and measurement as described above. Similarly, when the middle finger resting on the guiding surface 12 is punctured at a side of the fingertip, the user can slightly twist the finger to abut the finger against the aligning feature 11 of the biosensor 10 to get alignment with the test strip, without moving the biosensor 10. As described previously, the aligning feature 11 serves to fittingly receive and thereby position the finger. The aligning feature 11 in the present embodiments comprises two positioning blocks 111, and a distance between the two positioning blocks 111 is exactly the width of the guiding surface 12. For fittingly receiving the finger, the width of the guiding surface 12 is better limited to an extent making it suitable for this purpose. In particular, the width of the guiding surface is preferably of 1 to 3 centimeters, more preferably about 2 centimeters, and most preferably about 1.5 centimeters.

In another embodiment of the present invention, the aligning feature 11 may be such configured that the distance between the two positioning blocks 111 is adjustable. Such adjustment may be achieved by any means known in the art. For example, a sliding structure is provided, so that after the user's finger is placed on the guiding surface 12, the two positioning blocks 111 can be drawn together by means of the sliding structure and then fixed at the adjusted positions where a proper distance is defined therebetween by means of screws. Thereby, the biosensor 10 can have the guiding surface 12 adaptive to users of various finger sizes.

The inclined surface of the guiding surface 12 may further comprise with an audio output 13. The audio output 13 serves to display audio instructions based on an audio carrier or a chip loaded with audio files and audio drivers installed in the biosensor 10, thereby voicefully guiding the user to operate the biosensor 10 by following the prerecorded step-by-step instructions. Of course, the location of the audio output 13 is not limited to the inclined guiding surface 12 and the audio output 13 may be deposited at any other location on the biosensor 10, such as at the lateral or rear end of the cover 3 of the biosensor 10.

Furthermore, a removable chassis 17 may be deposited below the test-strip socket 18 of the biosensor 10. When using the biosensor 10, the user pulls the removable chassis 17 frontward and pushes it back into the biosensor 10 after use of the biosensor 10. It is a concern that when there is excessive blood continuously coming out, the blood may drop and contaminate the environment, or worse, endanger the next user with the risk of infectious diseases, such as hepatitis B. The removable chassis 17 thus serves to receive the excessive blood. After use, the removable chassis 17 is pulled out from the biosensor 10 to receive excessive blood and then be cleaned easily by wipe or wash.

Additionally, in another embodiment of the present invention, the cover 3 of the biosensor 10 further comprises a USB connecting port 16. Through the USB connecting port 16, the user's individual blood sugar levels can be transmitted to a personal computer, a remote monitoring system hosted by a medical service provider or other blood-sugar management application via a wire connection for graphically showing the user's full physiological data profile. Alternatively, the USB connecting port 16 may be replaced by an infrared transmitter or a blue-tooth device so as to transmit the physiological data stored in the biosensor 10 outward wirelessly.

With the biosensor 10 as described above, after using a disposable blood lancet or a blood-sampling pen to puncture his/her finger skin and squeezing the punctured finger to raise a drop of blood, a user can simply place the punctured finger on the guiding surface 12 of the biosensor 10 placed on the tabletop to make the finger aligned with the test strip 19 without lifting the biosensor 10 with the other hand. Since the blood drop can be precisely aligned with the window open to the test strip in virtue of the guidance of the guiding surface 12, even if the user is a greybeard or a person with hand tremor, he/she can operate the biosensor 10 with a single hand, and does not need to try hard to align the blood drop on his/her finger with the window open to the test strip 19 installed in the biosensor 10. Therefore, the biosensor 10 of the present invention overcomes the shortcomings of the existing biosensor and provides easy blood sugar measurement.

While the invention has been described by means of specific embodiments, numerous modifications and variations could be made thereto by those skilled in the art without departing from the scope and spirit of the invention set forth in the claims.

What is claimed is:

1. A biosensor with finger-positioning alignment structure, comprising:
   a bottom plate,
   a cover, wherein the cover mounted on the bottom plate has a front end provided with a guiding plate having a guiding surface for positioning a finger, and the guiding plate has a center line, in which the center line passes through a center of the guiding surface; and
   a test-strip socket, which is formed at the front end of the cover below the guiding surface to aid in structural alignment of a finger on the test-strip socket;
   wherein a removable chassis is deposited below the test-strip socket.

2. The biosensor of claim 1, wherein the test-strip socket is formed on the center line of the guiding plate.

3. The biosensor of claim 1, wherein the guiding surface is inclined toward the test-strip socket.

4. The biosensor of claim 1, wherein the guiding plate at the front end of the cover has two opposite sides thereof formed as an aligning feature.

5. The biosensor of claim 4, wherein the aligning feature comprises two positioning blocks.

6. The biosensor of claim 5, wherein the positioning blocks comprises angled structures that are transversely symmetrical.

7. The biosensor of claim 1, wherein the cover further comprises a USB connecting port.

8. The biosensor of claim 1, wherein the guiding plate further comprises an audio output.

9. The biosensor of claim 1, wherein the guiding surface has a width ranging between 1 to 3 centimeters.

10. The biosensor of claim 9, wherein the guiding surface has a width of about 2 centimeters.

11. The biosensor of claim 10, wherein the guiding surface has a width of about 1.5 centimeters.

* * * * *